US00PP24302P2

(12) United States Plant Patent
Konst

(10) Patent No.: US PP24,302 P2
(45) Date of Patent: Mar. 11, 2014

(54) ***ALSTROEMERIA* PLANT NAME 'KONCASWEET'**

(50) Latin Name: *Alstroemeria hybrida*
Varietal Denomination: Koncasweet

(75) Inventor: Johannes Wilhelmus Maria Konst, Nieuwveen (NL)

(73) Assignee: Könst Breeding B.V., Nieuwveen (NL)

( * ) Notice: Subject to any disclaimer, the term of this patent is extended or adjusted under 35 U.S.C. 154(b) by 48 days.

(21) Appl. No.: 13/506,948

(22) Filed: May 25, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Koncasweet', characterized by its compact and mounding plant habit; sturdy and strong plants; vigorous growth habit; freely branching habit; numerous white and red-colored flowers; and good garden performance.

2 Drawing Sheets

Botanical designation: *Alstroemeria hybrida.*
Cultivar denomination: 'KONCASWEET'.

BACKGROUND OF THE INVENTION

The present invention relates to a new and distinct cultivar of *Alstroemeria* plant, botanically known as *Alstroemeria hybrida*, typically grown as a potted garden *Alstroemeria*, and hereinafter referred to by the name 'Koncasweet'.

The new *Alstroemeria* plant is a product of a planned breeding program conducted by the Inventor in Nieuwveen, The Netherlands. The objective of the breeding program is to create new compact potted garden *Alstroemeria* plants that flower early and freely with attractive leaf and flower coloration.

The new *Alstroemeria* plant originated from a cross-pollination made by the Inventor in Nieuwveen, The Netherlands on Jun. 11, 2007 of a proprietary *Alstroemeria hybrida* selection identified as code number 24096-2, not patented, as the female, or seed, parent with a proprietary *Alstroemeria hybrida* selection identified as code number 07-0-RD, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands on Sep. 7, 2009.

Asexual reproduction of the new *Alstroemeria* plant by in vitro rhizogenesis in a controlled greenhouse environment in Nieuwveen, The Netherlands since Sep. 7, 2009 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncasweet'. These characteristics in combination distinguish 'Koncasweet' as a new and distinct *Alstroemeria* plant:

1. Compact and mounding plant habit.
2. Sturdy and strong plants.
3. Vigorous growth habit.
4. Freely branching habit.
5. Numerous white and red-colored flowers.
6. Good garden performance.

Plants of the new *Alstroemeria* can be compared to plants of the female parent selection. Plants of the new *Alstroemeria* differ primarily from plants of the female parent selection in the following characteristics:

1. Plants of the new *Alstroemeria* are more compact than plants of the female parent selection.
2. Plants of the new *Alstroemeria* and the female parent selection differ in flower color as plants of the female parent selection have orange-colored flowers.

Plants of the new *Alstroemeria* can be compared to plants of the male parent selection. Plants of the new *Alstroemeria* differ primarily from plants of the male parent selection in flower color.

Plants of the new *Alstroemeria* can be compared to plants of the *Alstroemeria hybrida* 'Koncavanti', disclosed in U.S. Plant Pat. No. 22,283. In side-by-side comparisons conducted in Nieuwveen, The Netherlands, plants of the new *Alstroemeria* differed from plants of 'Koncavanti' in the following characteristics:

1. Plants of the new *Alstroemeria* were more compact than plants of 'Koncavanti'.
2. Plants of the new *Alstroemeria* had larger flowers than plants of 'Koncavanti'.
3. Plants of the new *Alstroemeria* and 'Koncavanti' differed in flower color as plants of 'Koncavanti' had pink-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Koncasweet' grown in container.

The photograph on the second sheet is a close-up view of a typical flowering plant of 'Koncasweet'.

DETAILED BOTANICAL DESCRIPTION

The aforementioned photographs and following observations and measurements describe plants of the new *Alstroemeria* grown during the spring in 19-cm containers in a glass-covered greenhouse in Nieuwveen, The Netherlands and under cultural practices typical of commercial potted *Alstroemeria* production. During the production of the plants, day temperatures ranged from 6° C. to 30° C. and night temperatures ranged from 6° C. to 16° C. Plants were 36 weeks old when the photographs and description were taken. In the following description, color references are made to The Royal Horticultural Society Colour Chart, 2001 Edition, except where general terms of ordinary dictionary significance are used.

Botanical classification: *Alstroemeria hybrida* 'Koncasweet'.

Parentage:

*Female, or seed, parent.*—Proprietary *Alstroemeria hybrida* selection identified as code number 24096-2, not patented.

*Male or pollen parent.*—Proprietary *Alstroemeria hybrida* selection identified as code number 07-0-RD, not patented.

Propagation:

*Type.*—In vitro rhizogenesis.

*Root description.*—Thick, fleshy; color, close to 159D.

*Rooting habit.*—Freely branching; dense.

*Rhizome description.*—Shape: Elongate; rounded. Length: About 5.5 cm. Diameter: About 1.2 cm. Texture: Smooth. Color: Close to 161D.

Plant description:

*Plant habit.*—Compact and mounded; freely branching habit, bushy appearance; sturdy and strong plants; vigorous growth habit.

*Plant height.*—About 18 cm.

*Plant diameter* (*area of spread*).—About 35 cm.

Stem description:

*Aspect.*—Upright and somewhat outwardly spreading.

*Internode length.*—About 0.3 cm to 1.2 cm.

*Strength.*—Strong, sturdy.

*Texture.*—Smooth, glabrous.

*Color.*—Close to 139C to 139D.

Foliage description:

*Arrangement.*—Alternate; below the peduncle, arranged in a single whorl; leaves sessile.

*Length.*—About 6 cm to 12.2 cm.

*Width.*—About 1.1 cm to 2.5 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to 137A. Developing leaves, lower surface: Close to 137C. Fully expanded leaves, upper surface: Close to 139A; venation, close to 139A. Fully expanded leaves, lower surface: Close to 137B; venation, close to 137A.

Flower description:

*Flower type and habit.*—Single cup-shaped flowers arranged in compound umbels; flowers face upright to outwardly; freely flowering habit; about four to 15 flowers per inflorescence; and about 40 to 80 flowers developing per plant.

*Natural flowering season.*—Flowering continuous from the late spring until the autumn in The Netherlands.

*Fragrance.*—None detected.

*Flower longevity on the plant.*—About one to three weeks; flowers not persistent.

*Flower longevity as a cut flower.*—About one to two weeks; flowers not persistent.

*Flower buds.*—Length: About 4 cm to 5 cm. Diameter: About 1.7 cm. Shape: Ovoid. Color: Close to 59A and 37C; towards the apex, close to 139B.

*Umbel height.*—About 11.5 cm.

*Umbel diameter.*—About 12.5 cm to 15 cm.

*Flower diameter.*—About 6.6 cm.

*Flower depth* (*height*).—About 6.4 cm.

*Perianth.*—Arrangement: Six arranged in two whorls, each whorl with two lateral and one median segments. Size, inner perianth: Length, lateral segments: About 6.5 cm. Width, lateral segments: About 1.9 cm. Length, median segment: About 5.6 cm. Width, median segment: About 1.8 cm. Size, outer perianth: Length, lateral segments: About 5.8 cm. Width, lateral segments: About 3.2 cm. Length, median segment: About 6.4 cm. Width, median segment: About 3.3 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Embedded point. Base, inner and outer perianths, lateral and median segments: Attenuate. Margin, inner and outer perianths, lateral and median segments: Entire; towards the apex, crenate to serrate. Texture, inner and outer perianths, lateral and median segments: Smooth, glabrous. Color, inner perianth: When opening, lateral segments, upper surface: Towards the apex, close to 139D; mid-section, close to 160D; towards the base, close to 75B; stripes, close to 187A. When opening, median segments, upper surface: Towards the apex, close to 139D; mid-section, close to 160D and 186B; towards the base, close to 75B; stripes, close to 187A. When opening, lateral segments, lower surface: Towards the apex, close to 139C; mid-section, close to 160D; towards the base, close to 58D; stripes, close to 201A. When opening, median segment, lower surface: Towards the apex, close to 139C; mid-section, close to 160D and 186C; towards the base, close to 58D; stripes, close to 201A. Fully opened, lateral segments, upper surface: Towards the apex, close to 139D; mid-section, close to 160D; towards the base, close to 75B; stripes, close to 187A. Fully opened, median segment, upper surface: Towards the apex, close to 139D; mid-section, close to 160D and 58A; towards the base, close to 75B; stripes, close to 187A.

Fully opened, lateral and median segments, lower surface: Towards the apex, close to 139C; mid-section, close to 160D; towards the base, close to 58D; stripes, close to 201A. Color, outer perianth: When opening, lateral and median segments, upper surface: Towards the apex, close to 138B; mid-section, close to 186B; towards the margin, close to 156D; towards the base, close to 76D. When opening, lateral and median segments, lower surface: Towards the apex, close to 138A; mid-section and base, close to 46A; margins, close to 156D; towards the base, close to 46A. Fully opened, lateral segments, upper surface: Towards the apex, close to 138B; mid-section, close to 186B; margins, close to 156D; towards the base, close to 75B. Fully opened, median segments, upper surface: Towards the apex, close to 138B; mid-section, close to 186B; margins, close to 156D; towards the base, close to 76B. Fully opened, lateral segments, lower surface: Towards the apex, close to 141 A; mid-section, close to 46A; margins, close to 156D; towards the base, close to 46A. Fully opened, median segments, lower surface: Towards the apex, close to 138A; mid-section, close to 46A; margins, close to 156D; towards the base, close to 46A.

*Pedicels.*—Length: About 0.8 cm to 2.5 cm. Diameter: About 2 mm to 3 mm. Strength: Strong. Angle: About 70° to 80° from vertical. Texture: Smooth, glabrous. Color: Close to 138A tinted with close to 183B.

*Reproductive organs.*—Stamens: Quantity per flower: Six. Anther shape: Oval. Anther size: About 2 mm by 6 mm. Anther color: Close to 199B. Pollen amount: Abundant. Pollen color: Close to 186B. Pistils: Quantity per flower: One. Pistil length: About 4.4 cm. Style length: About 3.8 cm. Style color: Close to N74A. Stigma color: Close to 73A. Ovary color: Close to 138A tinted with close to 183A.

*Fruits.*—Length: About 1.2 cm. Diameter: About 9 mm. Color: Close to 138A tinted with close to 183A.

*Seeds.*—Seed production has not been observed on plants of the new *Alstroemeria.*

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncasweet' as illustrated and described.

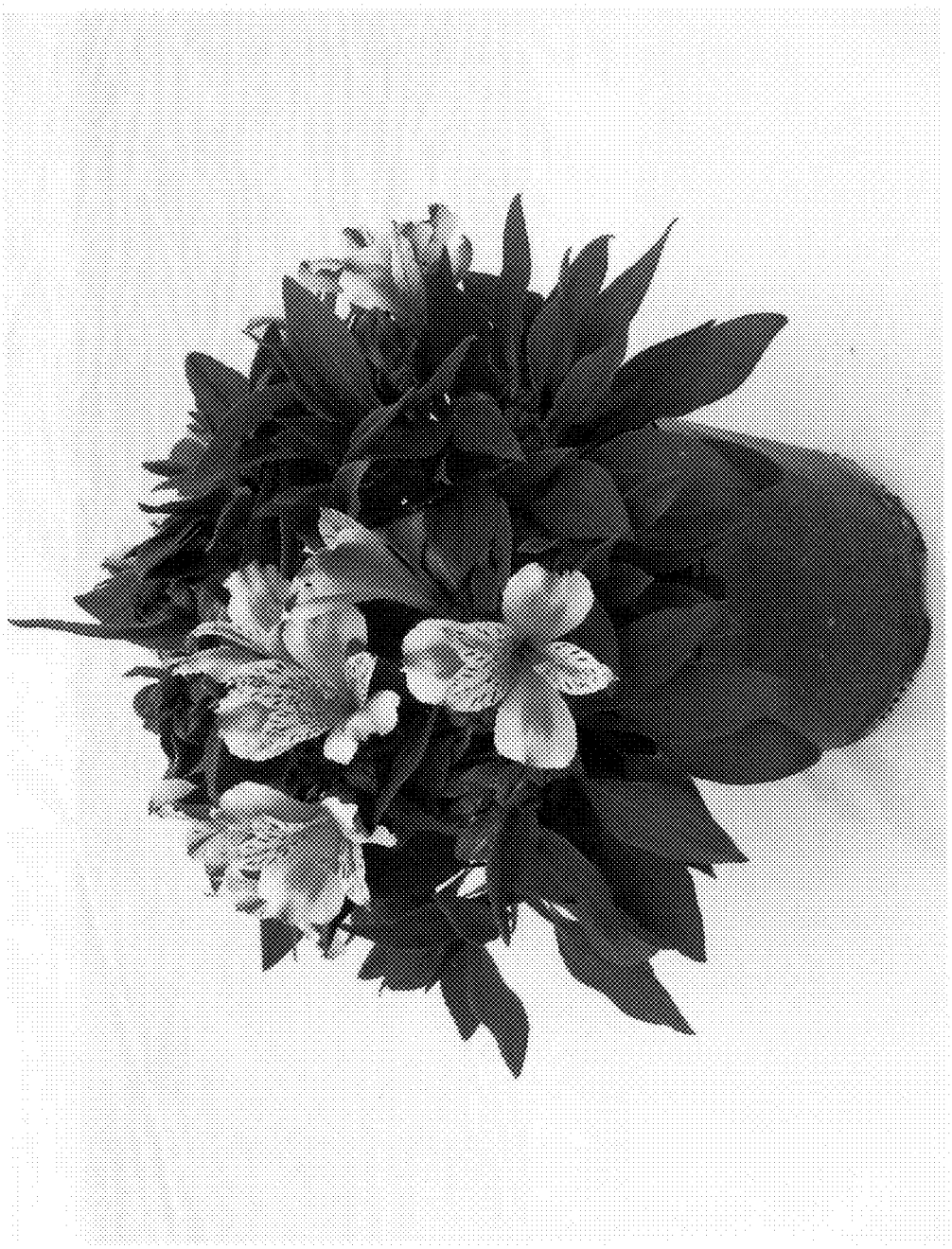

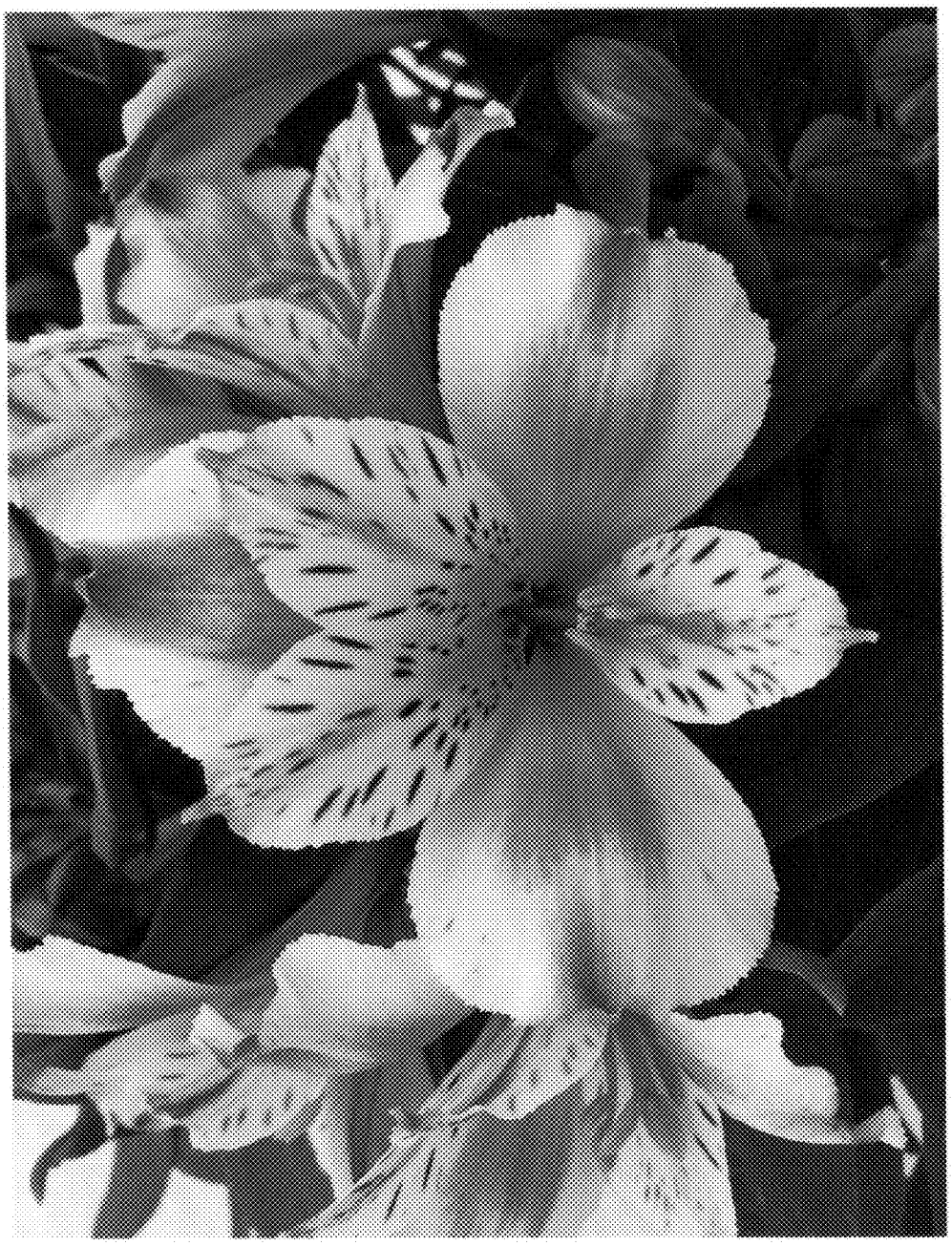

* * * * *